United States Patent
He et al.

(10) Patent No.: US 10,853,516 B2
(45) Date of Patent: Dec. 1, 2020

(54) METHODS AND APPARATUS USING HUMAN ELECTROCARDIOGRAM TO PROTECT ELECTRONIC DATA

(71) Applicant: INTEL CORPORATION, Santa Clara, CA (US)

(72) Inventors: Hua He, Shanghai (CN); Jixing Gu, Shanghai (CN); Ke Han, Shanghai (CN); Guoquan Shen, Shanghai (CN); Jesse Walker, Hillsboro, OR (US)

(73) Assignee: INTEL CORPORATION, Santa Clara, CA (US)

( * ) Notice: Subject to any disclaimer, the term of this patent is extended or adjusted under 35 U.S.C. 154(b) by 280 days.

(21) Appl. No.: 15/773,832

(22) PCT Filed: Dec. 9, 2015

(86) PCT No.: PCT/CN2015/096758
§ 371 (c)(1),
(2) Date: May 4, 2018

(87) PCT Pub. No.: WO2017/096550
PCT Pub. Date: Jun. 15, 2017

(65) Prior Publication Data
US 2018/0330116 A1   Nov. 15, 2018

(51) Int. Cl.
*G06F 21/32* (2013.01)
*G06F 21/62* (2013.01)
(Continued)

(52) U.S. Cl.
CPC ...... *G06F 21/6245* (2013.01); *A61B 5/04012* (2013.01); *G06F 21/31* (2013.01);
(Continued)

(58) Field of Classification Search
CPC ....... G06F 21/32; G06F 21/62; G06F 21/6245
See application file for complete search history.

(56) References Cited

U.S. PATENT DOCUMENTS

| 2009/0037743 A1* | 2/2009 | Narayanaswami ... H04L 9/3231 |
| | | 713/186 |
| 2011/0154023 A1* | 6/2011 | Smith ..................... G06F 21/78 |
| | | 713/155 |

(Continued)

FOREIGN PATENT DOCUMENTS

| CN | 103944645 A | 7/2014 |
| CN | 104239869 A | 12/2014 |

(Continued)

OTHER PUBLICATIONS

Sriram et al., "Activity-aware ECG-based patient authentication for remote health monitoring", 8 pages (Year: 2009).*

(Continued)

*Primary Examiner* — Thaddeus J Plecha
(74) *Attorney, Agent, or Firm* — Jaffery Watson Mendonsa & Hamilton LLP (57) ABSTRACT

In a method for protecting electronic data, a data processing system (20, 20A, 20B) uses (a) a master electrocardiogram (ECG) identifier (44) for an authorized user of the system and (b) a secret chip key (26) for the system to encrypt data in the system. Also, before allowing the encrypted data to be decrypted, the system collects an ECG reading for a current user of the system and uses (a) the collected ECG reading for the current user and (b) at least one predetermined ECG identifier (EID) vector for the authorized user to determine whether the current user is the authorized user. In response to determining that the current user is the authorized user, the system uses the master ECG identifier (44) for the authorized user and the secret chip key (26) for the system to decrypt the data.

25 Claims, 5 Drawing Sheets

(51) Int. Cl.
    *H04L 9/06*          (2006.01)
    *A61B 5/04*          (2006.01)
    *G06F 21/31*        (2013.01)

(52) U.S. Cl.
    CPC .............. *G06F 21/32* (2013.01); *G06F 21/62* (2013.01); *H04L 9/06* (2013.01); *H04L 2209/88* (2013.01)

(56) References Cited

U.S. PATENT DOCUMENTS

| | | | |
|---|---|---|---|
| 2012/0016827 A1* | 1/2012 | Evans | G07C 9/37 706/14 |
| 2013/0190635 A1* | 7/2013 | Shen | G06K 9/00503 600/521 |
| 2013/0307670 A1* | 11/2013 | Ramaci | G06F 21/32 340/5.82 |
| 2015/0304101 A1 | 10/2015 | Gupta et al. | |
| 2016/0044445 A1 | 2/2016 | Hu et al. | |
| 2016/0063233 A1* | 3/2016 | Bae | A61B 5/0456 726/19 |

FOREIGN PATENT DOCUMENTS

| | | |
|---|---|---|
| CN | 104299133 A | 1/2015 |
| WO | WO2006059190 | 6/2006 |

OTHER PUBLICATIONS

Sung et al., "ECG Authentication in Post-Exercise Situation", pp. 446-449 (Year: 2017).*
PCT Search Report and Written Opinion for PCT/CN2015/096758, completed Aug. 29, 2016.

\* cited by examiner

METHODS AND APPARATUS USING HUMAN ELECTROCARDIOGRAM TO PROTECT ELECTRONIC DATA

CROSS REFERENCE TO RELATED APPLICATIONS

The present application claims priority to and is a national stage entry under 35 USC § 371(b) of International Application No. PCT/CN2015/096758, which was filed Dec. 9, 2015, entitled "METHODS AND APPARATUS USING HUMAN ELECTROCARDIOGRAM TO PROTECT ELECTRONIC DATA."

TECHNICAL FIELD

This disclosure describes embodiments related to computer security. In particular, these embodiments relate to methods and apparatus that use human electro car diagram (ECG) information and other context information to protect electronic data.

BACKGROUND

As technology advances, mobile devices are becoming increasingly popular, and they are being used to store increasing amounts and types of valuable information. For instance, the data in a mobile device may include personal identifiers (IDs), bank information, address books, personal photos, premium content from service providers, and many other types of valuable and/or sensitive data. For purposes of this disclosure, the electronic data in a data processing system may be referred to in general as user data or sensitive data.

As described in greater detail below, the present disclosure introduces methods and apparatus that use data pertaining to a human heartbeat to encrypt user data.

DESCRIPTION OF EMBODIMENTS

Although humans generally have similar heart beats, there are distinct physiological differences between the heartbeats of different people. For instance, differences may be evident in characteristic which include, without limitation, the exact size and position of the waveform inflection points and/or the durations of particular portions within a heart rhythm.

According to the 2001 article entitled "ECG Analysis: A New Approach in Human Identification" by L. Biel et al., it is possible "to identify persons from a predetermined group" by using "[ECG] analysis." And according to the 2013 article entitled "Exploring Heartbeat Sub-patterns for Person Identification" by Carlos Carreiras et al., "Nesearch done to date has reinforced the potential of [ECG] signals in biometric applications."

Furthermore, according to the present disclosure, a data processing system may use data pertaining to a human heartbeat to encrypt user data. For instance, the data processing system may derive ECG data based on heartbeat data collected from an authorized user, and the data processing system may use that ECG data as a parameter to the encryption process. Consequently, the encrypted data may be tied to that authorized user. In addition, as described in greater detail below, as another parameter to the encryption process, the data processing system may use a secret chip key that is unique to the data processing system. Consequently, the encrypted data may also be tied to that particular data processing system.

Figure 1:
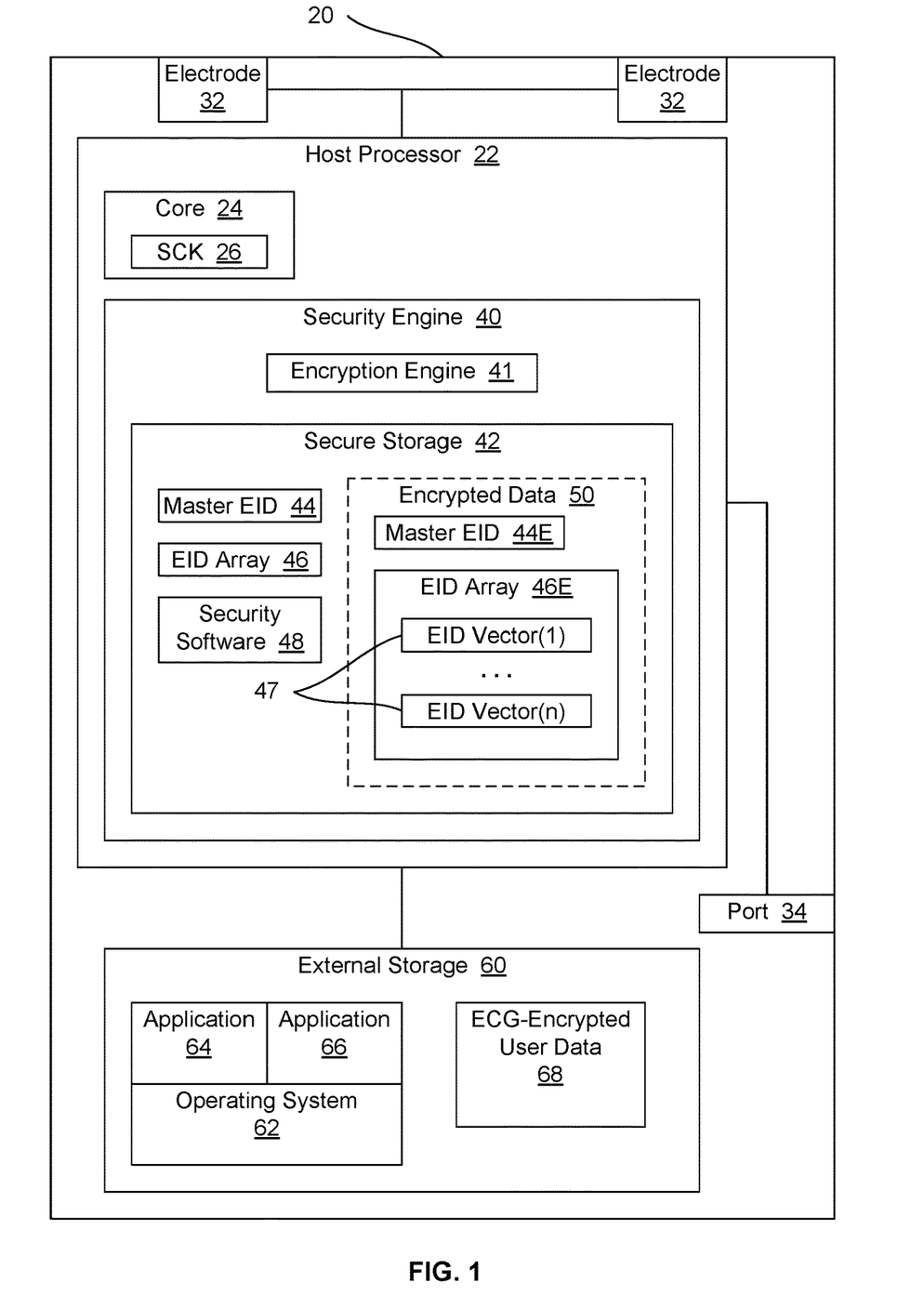
FIG. 1 is a block diagram of an example data processing system with technology for using human ECG data to protect sensitive data.

FIG. 1 is a block diagram of an example data processing system 20 with technology for using human ECG data to protect sensitive data. Data processing systems according to the present disclosure may be implemented as smartphones, tablets, laptop computers, or in any other suitable form factor. In the embodiment of FIG. 1, data processing system 20 includes a host processor 22 in communication with external storage 60, port 34, and electrodes 32. Host processor 22 includes a processing core 24 and a security engine 40. Security engine 40 may also be referred to as a security controller. Also, electrodes 32 may also be referred to as ECG pads.

Security engine 40 includes an encryption engine 41 and secure storage 42. Encryption engine 41 may be implemented as a hardware module. Secure storage 42 includes security software 48. As described in greater detail below, data processing system 20 uses security software 48 to perform operations such as collecting ECG data from the current user, verifying the current user, using ECG data to encrypt sensitive information, etc.

Core 24 includes a secret chip key (SCK) 26. SCK 26 is a unique, predetermined value that the manufacturer of processor 22 writes or fuses into core 24 when processor 22 is being manufactured. Thus, each different processor produced by the manufacturer get a different SCK, and the manufacturer keeps those values secret. In addition, processor 22 is designed to prevent any host software from ever being able to read SCK 26. Thus, SCK 26 is never transmitted through any application programming interface (API) calls, and SCK 26 is completely hidden from all host software.

However, as described in greater detail below, security engine 40 may access SCK 26 for use as an internal parameter to an encryption process to be performed by encryption engine 41. For instance, as described in greater detail below, security software 48 may pass a plaintext payload and ECG data to encryption engine 41. In other words, security software 48 may inject the data to be encrypted. Encryption engine 41 may then use that ECG data along with SCK 26 to encrypt the payload. Thus, security hardware uses SCK 26 to encrypt the data, but SCK 26 itself is never revealed to any software components.

Host processor 22 may be implemented as a system on a chip (SOC). Also, SCK 26 may be referred to as a chip unique key.

External storage 60 may include host software such as an operating system (OS) 62 and various applications 64 and 66. As described in greater detail below, once security software 48 has encrypted sensitive data using ECG data, external storage 60 may also include the resulting ECG-encrypted user data 68.

In one embodiment, application 64 is a health tracking or fitness application that is designed to monitor the heartbeat of the user via electrodes 32.

Figure 2:
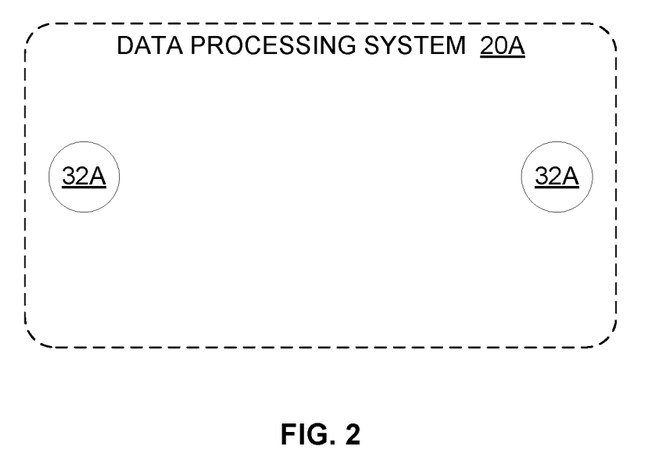
FIGS. 2 and 3 are schematic diagrams of example data processing systems with technology for using human ECG data to protect sensitive data.
Figure 3:
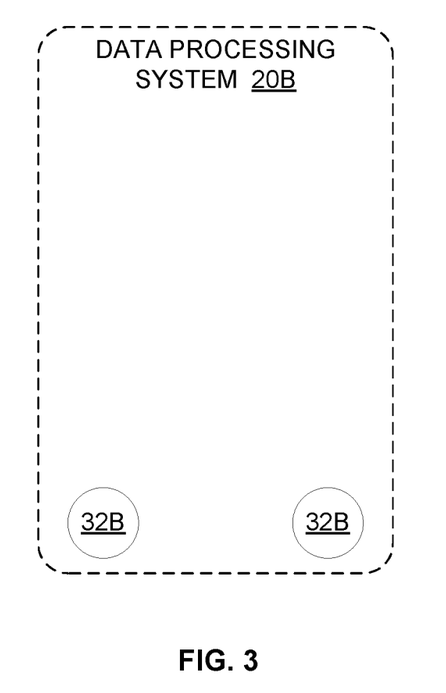

FIGS. 2 and 3 are schematic diagrams of example data processing systems with technology for using human ECG data to protect sensitive data. In particular, FIG. 2 depicts a data processing system 20A with a rectangular case having short side edges and longer top and bottom edges. Also, in the embodiment of FIG. 2, the electrodes 32A are positioned on the back of the case, spaced widely apart near the midline of the case. By contrast, FIG. 3 depicts a data processing system 20B with the electrodes 32B positioned on the back of the case near the bottom edge. The electrodes may be placed in other suitable locations in other embodiments.

Figure 4:
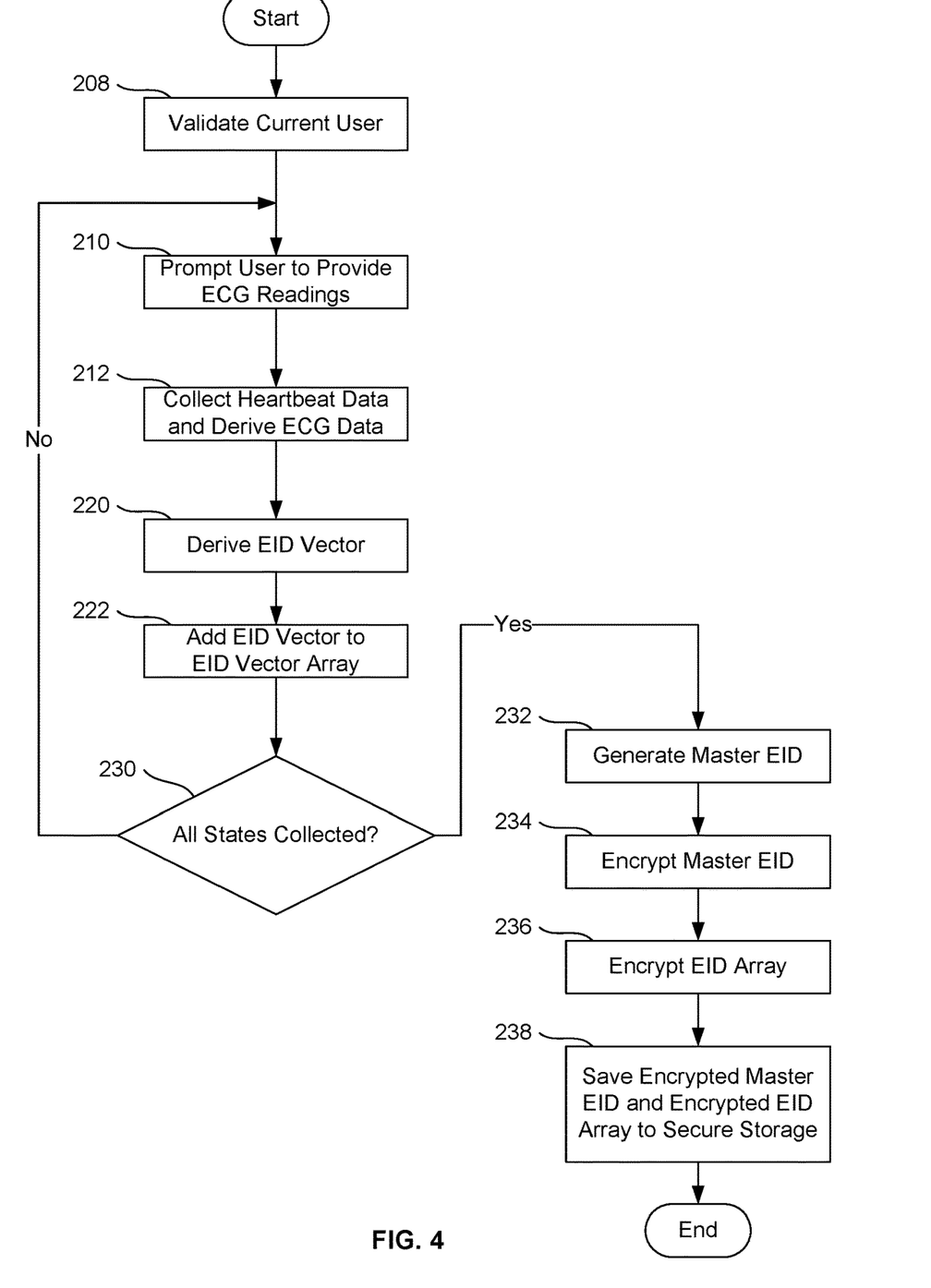
FIG. 4 presents a flowchart of an example process for configuring a data processing system with ECG data for a user.

FIG. 4 presents a flowchart of an example process for configuring data processing system 20 with ECG data for a user. As described in greater detail below, during that initialization process, data processing system 20 may capture ECG data from a user and extract an ECG identifier (ID) for that user. (An ECG ID may also be referred to as an EID.) This initialization process may be used, for example, as part of the process for defining an authorized user for data processing system 20, or in response to ECG encryption being enabled or initiated for data processing system 20.

As shown at block 208, the process of FIG. 4 may start with security software 48 in data processing system 20 validating the current user. For instance, the current user may be required to enter a password to verify his or her identity. Then, as shown at block 210, after successful validation of the user, security software 48 may prompt the user to provide ECG readings.

In particular, security software 48 may require the user to provide ECG readings for a series of different physical states for various common scenarios. Those states may include (a) a newly awaked state, when the user has just gotten out of bed; (b) a calm state; (c) an active state, when the user is exercising, and (d) any other suitable states. As described in greater detail below and illustrated in FIG. 1, security software 48 may then save ECG data pertaining to each of those states in an ECG identifier (EID) array 46.

Referring again to block 210 of FIG. 4, security software 48 may first prompt the user to provide ECG readings for a newly awakened state. As shown at block 212, security software 48 may then monitor electrodes 32 to collect raw heartbeat data from the user. As shown at block 212, security software 48 may also derive ECG data from that heartbeat data. For instance, for the derived ECG data, security software 48 may save a set of values characterizing various different aspects of an ECG. Those aspects may include, without limitation:

- metrics for one or more characteristics of a detected atrial depolarization (which may be referred to as a "P wave");
- metrics for one or more characteristics of a detected ventricular depolarization (which may be referred to as a "QRS complex"); and
- metrics for one or more characteristics of a detected ventricular repolarization (which may be referred to as a "T wave").

Security software 48 may require a certain number of heartbeats to be collected in each state. The data that security software 48 saves to characterize a single heartbeat may be referred to as an ECG vector. As shown at block 220, once security software 48 has collected ECG vectors for enough heartbeats for the current state, security software 48 may then derive an EID vector for the user for the current state. In one embodiment, security software 48 derives the EID vector for the current state by averaging all of the ECG vectors that were collected for that state. For instance, the EID vector may include the average value of one or more metrics pertaining to the P wave, the average value of one or more metrics pertaining to the QRS complex, etc. In other embodiments, the security software 48 may user other techniques for generating the EID vector.

As shown at block 222, security software 48 may then add the generated EID vector to EID array 46. As shown at block 230, security software 48 may then determine whether EID vectors have been generated for all necessary physical states. If data has not been collected for all states, the process may return to block 210, with security software 48 prompting the user to provide ECG readings for the next physical state (e.g., a calm state). The data collection process may then proceed for that state as described above.

Once security software 48 has populated EID array 46 with EID vectors 47 for all required physical states, the process may flow from block 230 to claim 232, which shows security software 48 generating a master ECG ID (i.e., a master EID) for the user, based on some or all of the data in EID array 46. For instance, security software 48 may compute the master EID 44 as the average of the EID vectors in EID array 46. Alternatively, security software 48 may select one of the EID vectors (e.g., the calm EID vector) to serve as master EID 44. Master EID 44 may also be referred to as EID0.

As shown at blocks 234 and 236, security software 48 may then encrypt master EID 44 and EID array 46, thereby generating encrypted versions of those values. As shown at block 238, security software 48 may then save those encrypted values in secure storage 42. Consequently, as shown in FIG. 1, secure storage 42 includes encrypted data 50, and that encrypted data includes the encrypted version of the master EID (denoted with reference number 44E) and the encrypted version of the EID array (denoted with reference number 46E). The process of FIG. 4 may then end.

In one embodiment, to encrypt master EID 44 and EID array 46, security software 48 uses the Advanced Encryption Standard (AES) protocol. In addition, security software 48 uses SCK 26 as the AES master key. Further, security software 48 may use encryption engine 41 to perform the encryption. Also, security software 48 may then delete the unencrypted versions of the master EID and the EID array from secure storage 42, so that no plaintext master EID is stored anywhere when it is not being used by security software 48, and the encrypted master EID is stored inside secure storage, rather than in an OS file system.

Figure 5A:
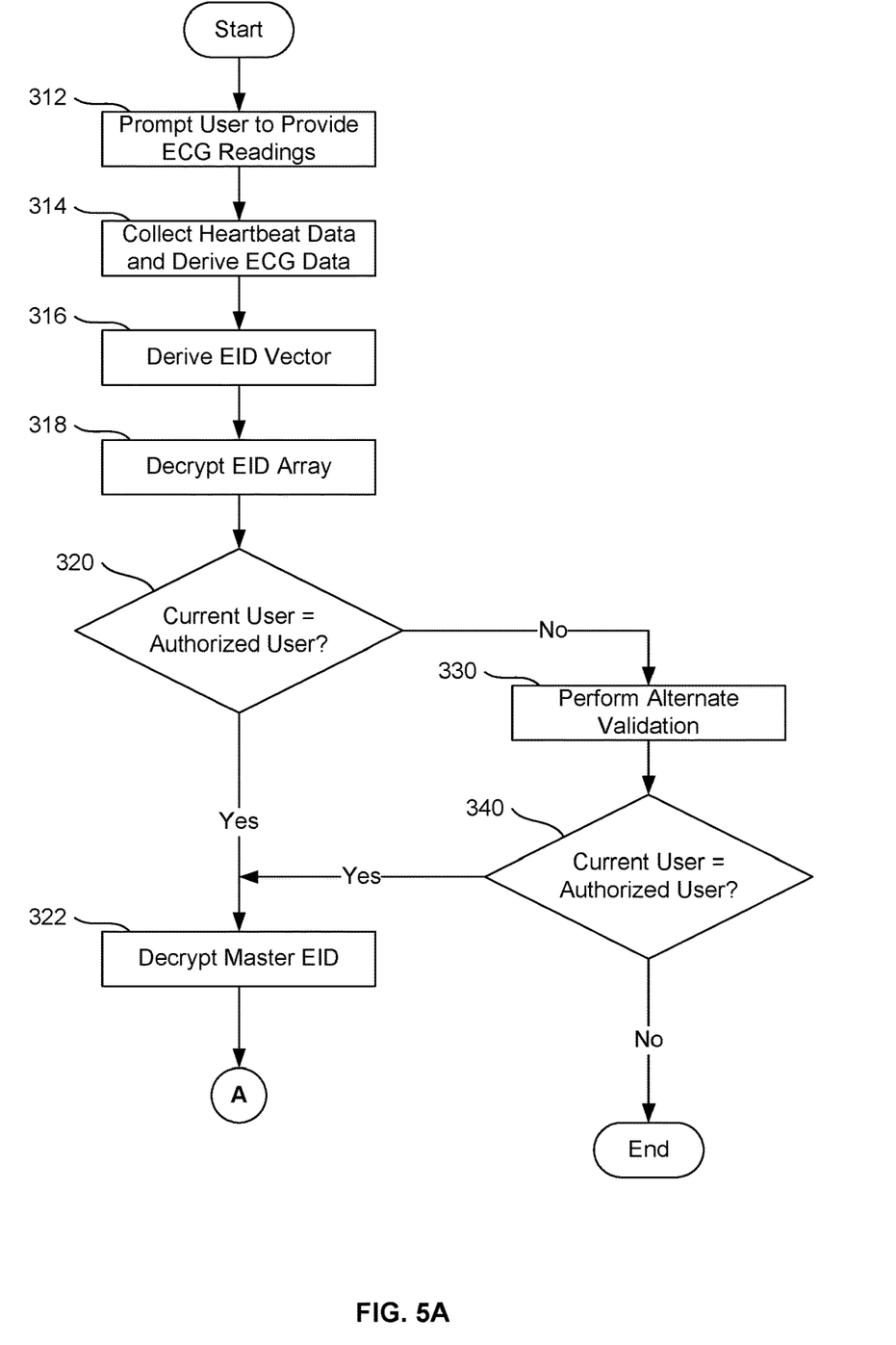
FIGS. 5A and 5B present a flowchart of an example process for using ECG data to protect user data.
Figure 5B:
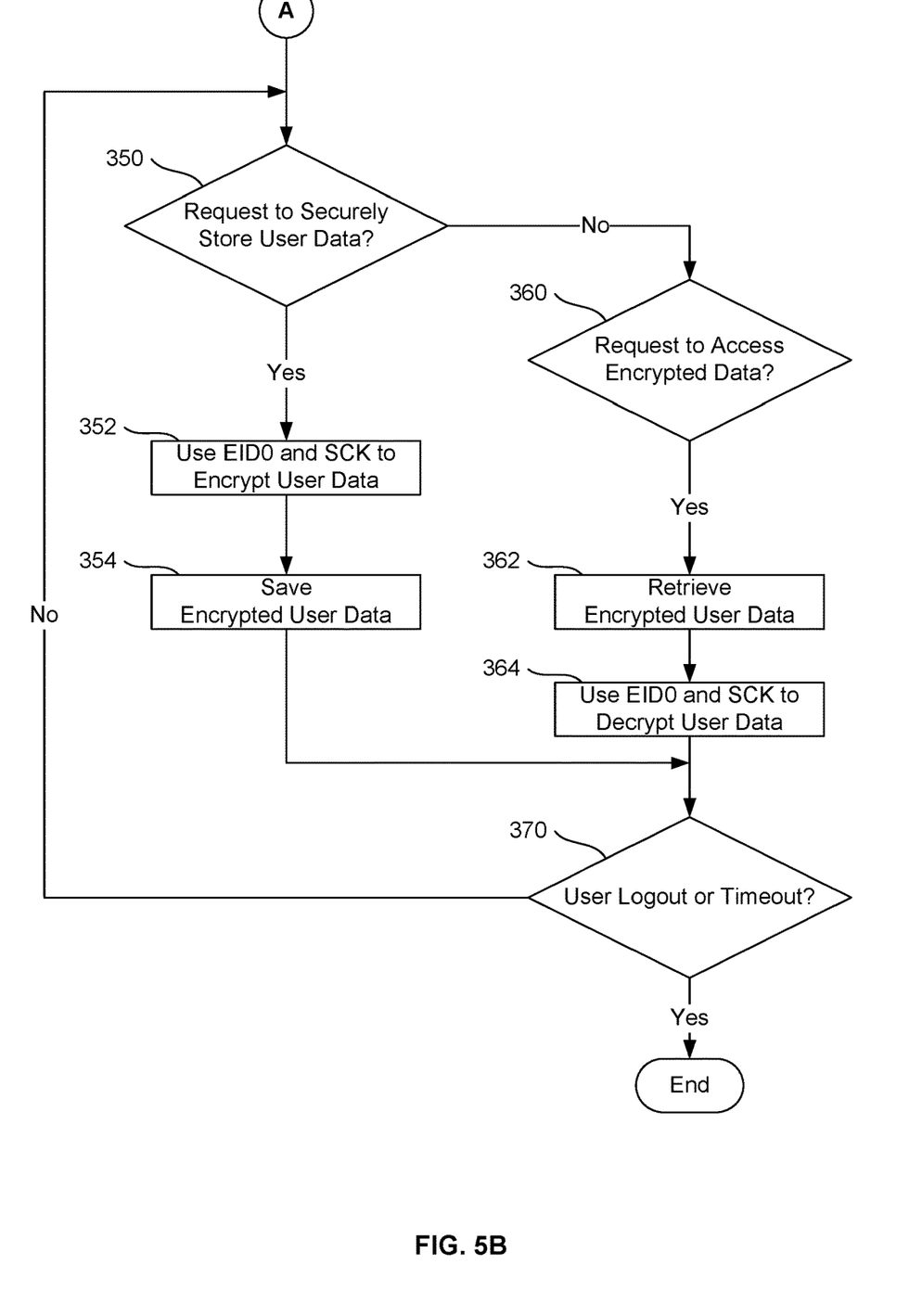

FIGS. 5A and 5B present a flowchart of an example process for using ECG data to protect data. That process may start after data processing system 20 has been initialized with master EID 44 and EID array 46 for the authorized user. In particular, the process of FIG. 5A may start with security software 48 validating the current user, as shown at blocks 312 through 320. For instance, at block 312 security software 48 may prompt the current user to provide ECG readings. At block 314 security software 48 may then collect heartbeat data from the current user via electrodes 32. Security software 48 may also derive ECG data from that heartbeat data. As shown at block 316, security software 48 may then derive an EID vector for the current user, based on the derived ECG data. For instance, security software 48 may generate that EID vector by averaging the ECG data for multiple heartbeats.

In addition, as shown at block 318, security software 48 may recreate EID array 46 for the authorized user by decrypting EID array 46E. For instance, security software 48 may use encryption engine 41 and SCK 26 to decrypt EID array 46E. As shown at block 320, security software 48 may then compare the EID vector for the current user with EID vectors 47 for the authorized user, to determine whether the current user is the authorized user. For instance, security software 48 may utilize ECG-vector correlation-difference calculations to authenticate user identity.

Thus, by using ECG data, security software 48 may validate the current user without requiring him or her to enter a password. However, if the current user fails ECG validation, the process may pass to block 330, to give the current user an option to perform a different type of user validation. For instance, at block 330 security software 48 may allow the current user to enter a password to validate that the current user is the authorized user. However, as shown at block 340, if the current user also fails the alternate validation, the process may abort or exit.

If the current user passes validation, however, security software 48 may then recreate master EID 44 by decrypting master EID 44E in block 322. For instance, security software 48 may use encryption engine 41 and SCK 26 to decrypt master EID 44E. The process may then pass through page connector A to FIG. 5B.

As shown at block 350, security software 48 may then determine whether any software has requested secure storage of user data. If secure storage of user data has been requested, security software 48 may use master EID 44 (also known as EID0) and SCK 26 to encrypt that user data in block 352. For instance, security software 48 may invoke encryption engine 41, instructing encryption engine 41 to use SCK 26 as the AES master key and to use master EID 44 as the initialization vector (IV) to encrypt the user data. Security software 48 may thus generate ECG-encrypted user data 68. As shown at block 354, security software 48 may then save ECG-encrypted user data 68 to any desired location. For instance, as shown in FIG. 1, security software 48 may store ECG-encrypted user data 68 in external storage 60. In addition or alternatively, security software 48 may cause ECG-encrypted user data 68 to be saved to remote storage. For instance, security software 48 may use port 34 to save ECG-encrypted user data 68 to the cloud via the Internet.

However, referring again to block 350, if software has not requested secure storage of user data, security software 48 may determine whether any software has requested access to encrypted data, as shown at block 360. As shown at block 362, if software has requested access to encrypted data, security software 48 may retrieve that encrypted data. And as shown at block 364, security software 48 may then decrypt that data. For instance, security software 48 may invoke encryption engine 41, instructing encryption engine 41 to use SCK 26 as the AES master key and to use master EID 44 as the IV to decrypt the data. Security software 48 may then make the decrypted data available to the software that requested it.

As shown at block 370, security software 48 may then determine whether the user has logged out or timed out. If so, the process may end. Otherwise, the process may return to block 350, with security software 48 processing requests to securely store data and requests to access encrypted data, as described above. Once the user has logged out or timed out, the process of FIG. 5B may end.

As a result, ECG-encrypted user data 68 in external storage 60 can only be interpreted by the device that created it, when that device is being operated by authorized user (e.g., the owner) of that device. In addition, if the data is stored in cloud, the data will be free of worry for cloud security as well.

In addition, the authorized user may validate his identity and access the protected data without typing a password each time. For example, before getting data encrypted or decrypted, the user may simply hold two fingers on the ECG pads, and security software 48 may captured ECG waveform data for the user from those fingers. Security software 48 may then extract the ECG-biometrics attributes vector from that data, and security software 48 may compare that vector against the predetermined EID vector array. For example, security software 48 may determine whether the current user is the authorized user by performing correlation analysis between the EID vector for the current user and predetermined vectors in EID array 46 to determine whether there is sufficient correlation to conclude that the ECG patterns match.

As has been described, after the user passes user authentication, the data to be encrypted or decrypted is sent to an encryption/decryption module, such as encryption engine 41. For instance, security software 48 may instruct encryption engine 41 to use ECG biometric data as an AES IV and SCK 26 as an AES master key.

For purposes of illustration, the present disclosure describes one or more example embodiments, but the present teachings are not limited to those particular embodiments. Other configurations are contemplated. Furthermore, the term "Internet of things" (IoT) refers to a system of devices that allows people to connect with remote objects. Data processing systems according to the present disclosure may be considered part of the IoT.

In light of the principles and example embodiments described and illustrated herein, it will be recognized that the illustrated embodiments can be modified in arrangement and detail without departing from such principles. Also, even though expressions such as "an embodiment," "one embodiment," "another embodiment," or the like are used herein, these phrases are meant to generally reference embodiment possibilities, and are not intended to limit the invention to particular embodiment configurations. As used herein, these phrases may reference the same embodiment or different embodiments, and those embodiments are combinable into other embodiments.

Any suitable operating environment and programming language (or combination of operating environments and programming languages) may be used to implement components described herein. As indicated above, the present teachings may be used to advantage in many different kinds of data processing systems. Example data processing systems include, without limitation, distributed computing systems, supercomputers, high-performance computing systems, computing clusters, mainframe computers, minicomputers, client-server systems, personal computers (PCs), workstations, servers, portable computers, laptop computers, tablet computers, personal digital assistants (PDAs), telephones, smartphones, handheld devices, wearable devices, entertainment devices such as audio devices, video devices, audio/video devices (e.g., televisions and set top boxes), vehicular processing systems, and other devices for processing or transmitting information. Accordingly, unless explicitly specified otherwise or required by the context, references to any particular type of data processing system (e.g., a wearable device) should be understood as encompassing other types of data processing systems, as well. Also, unless expressly specified otherwise, components that are described as being coupled to each other, in communication with each other, responsive to each other, or the like need not be in continuous communication with each other and need not be directly coupled to each other. Likewise, when one component is described as receiving data from or sending data to another component, that data may be sent or received through one or more intermediate components, unless expressly specified otherwise. In addition, some components of the data processing system may be implemented as adapter cards with interfaces (e.g., a connector) for communicating with a bus. Alternatively, devices or components may be implemented as embedded controllers, using components such as programmable or non-programmable logic devices or arrays, application-specific integrated circuits (ASICs), embedded computers, smart cards, and the like. For purposes of this disclosure, the term "bus" includes pathways that may be shared by more than two devices, as well as point-to-point pathways. Also, for purpose of this disclosure, a processor may also be referred to as a processing unit, a processing element, a central processing unit (CPU), etc.

This disclosure may refer to instructions, functions, procedures, data structures, application programs, microcode, configuration settings, and other kinds of data. As described above, when the data is accessed by a machine or device, the machine or device may respond by performing tasks, defining abstract data types or low-level hardware contexts, and/or performing other operations. For instance, data storage, random access memory (RAM), and/or flash memory may include various sets of instructions which, when executed, perform various operations. Such sets of instructions may be referred to in general as software. In addition, the term "program" may be used in general to cover a broad range of software constructs, including applications, routines, modules, drivers, subprograms, processes, and other types of software components. Also, applications and/or other data that are described above as residing on a particular device in one example embodiment may, in other embodiments, reside on one or more other devices. And computing operations that are described above as being performed on one particular device in one example embodiment may, in other embodiments, be executed by one or more other devices.

It should also be understood that the hardware and software components depicted herein represent functional elements that are reasonably self-contained so that each can be designed, constructed, or updated substantially independently of the others. In alternative embodiments, many of the components may be implemented as hardware, software, or combinations of hardware and software for providing the functionality described and illustrated herein. For example, alternative embodiments include machine accessible media encoding instructions or control logic for performing the operations of the invention. Such embodiments may also be referred to as program products. Such machine accessible media may include, without limitation, tangible storage media such as magnetic disks, optical disks, RAM, read only memory (ROM), etc., as well as processors, controllers, and other components that include RAM, ROM, and/or other storage facilities. For purposes of this disclosure, the term "ROM" may be used in general to refer to non-volatile memory devices such as erasable programmable ROM (EPROM), electrically erasable programmable ROM (EEPROM), flash ROM, flash memory, etc. In some embodiments, some or all of the control logic for implementing the described operations may be implemented in hardware logic (e.g., as part of an integrated circuit chip, a programmable gate array (PGA), an ASIC, etc.). In at least one embodiment, the instructions for all components may be stored in one non-transitory machine accessible medium. In at least one other embodiment, two or more non-transitory machine accessible media may be used for storing the instructions for the components. For instance, instructions for one component may be stored in one medium, and instructions another component may be stored in another medium. Alternatively, a portion of the instructions for one component may be stored in one medium, and the rest of the instructions for that component (as well instructions for other components), may be stored in one or more other media. Instructions may also be used in a distributed environment, and may be stored locally and/or remotely for access by single or multi-processor machines.

Also, although one or more example processes have been described with regard to particular operations performed in a particular sequence, numerous modifications could be applied to those processes to derive numerous alternative embodiments of the present invention. For example, alternative embodiments may include processes that use fewer than all of the disclosed operations, process that use additional operations, and processes in which the individual operations disclosed herein are combined, subdivided, rearranged, or otherwise altered.

In view of the wide variety of useful permutations that may be readily derived from the example embodiments described herein, this detailed description is intended to be illustrative only, and should not be taken as limiting the scope of coverage.

The following examples pertain to further embodiments.

Example A1 is a data processing system to support protection of electronic data. The data processing system comprises (a) one or more electrodes capable of receiving heartbeat signals from a user of the data processing system; (b) a processor in communication with the electrodes; (c) external storage responsive to the processor; and (d) security software. When the security software is executed by the processor, the security software enables the data processing system to use (a) a master ECG identifier for an authorized user of the data processing system and (b) a secret chip key for the data processing system to generate ECG-encrypted data. The security software also enables the data processing system to store the ECG-encrypted data in the external storage. The security software also enables the data processing system to, in response to a request for a decrypted version of the ECG-encrypted data, (i) use the one or more electrodes to collect at least one ECG reading for a current user of the data processing system; (ii) use (a) the collected ECG reading for the current user and (b) at least one predetermined EID vector for the authorized user to determine whether the current user is the authorized user; and (iii) in response to determining that the current user is the authorized user, use the master ECG identifier for the authorized user and the secret chip key for the data processing system to decrypt the ECG-encrypted data.

Example A2 is a data processing system according to Example A1, wherein the security software further enables the data processing system to save a collection of predetermined EID vectors for the authorized user. That collection of predetermined EID vectors comprises the at least one predetermined EID vector for the authorized user.

Example A3 is a data processing system according to Example A2, wherein the security software further enables the data processing system to prompt the authorized user to provide ECG readings for different physical states of the authorized user, wherein the different physical states comprise a resting state and an active state. Also, the collection of predetermined EID vectors for the authorized user is based on ECG readings taken from the authorized user in the different physical states.

Example A4 is a data processing system according to Example A2, wherein the data processing system further comprises secure storage responsive to the processor. Also, the security software further enables the data processing system to (a) save the master ECG identifier for the authorized user in the secure storage; (b) encrypt the collection of predetermined EID vectors for the authorized user; and (c) save the encrypted collection of predetermined EID vectors for the authorized user in the secure storage. Example A4 may also include the features of Example A3.

Example A5 is a data processing system according to Example A2, wherein the operation of using the collection of predetermined EID vectors for the authorized user to determine whether the current user is the authorized user comprises using ECG-vector correlation-difference calculations to determine whether the current user is the authorized user. Example A5 may also include the features of any one or more of Examples A3 and A4.

Example A6 is a data processing system according to Example A1, wherein the data processing system further comprises secure storage responsive to the processor. Also, the security software further enables the data processing system to (a) save, in the secure storage, a collection of predetermined EID vectors for the authorized user; and (b) generate the master ECG identifier for the authorized user, based on the collection of predetermined EID vectors for the authorized user. Example A6 may also include the features of any one or more of Examples A2 through A5.

Example A7 is a data processing system according to Example A6, wherein the operation of generating the master ECG identifier for the authorized user, based on the collection of predetermined EID vectors for the authorized user, comprises calculating the master ECG identifier as an average of the collection of predetermined EID vectors. Example A7 may also include the features of any one or more of Examples A2 through A5.

Example A8 is a data processing system according to Example A1, wherein the operation of using the one or more electrodes to collect an ECG reading for a current user of the data processing system comprises (a) receiving heartbeat signals from the current user; (b) deriving ECG information from the received heartbeat signals; and (c) generating an EID vector for the current user, based on the derived ECG information. Example A8 may also include the features of any one or more of Examples A2 through A7.

Example A9 is a data processing system according to Example A1, wherein the processor is configured to prevent host software from reading the secret chip key. Example A9 may also include the features of any one or more of Examples A2 through A7.

Example B1 is an apparatus to support protection of electronic data. The apparatus comprises a non-transitory machine accessible medium and security software in the machine accessible medium. When the security software is accessed by a processor of a data processing system, the security software enables the data processing system touse (a) a master ECG identifier for an authorized user of the data processing system and (b) a secret chip key for the data processing system to generate ECG-encrypted data. The security software also enables the data processing system to store the ECG-encrypted data in external storage. The security software also enables the data processing system to, in response to a request for a decrypted version of the ECG-encrypted data, (i) collect at least one ECG reading for a current user of the data processing system; (ii) use (a) the collected ECG reading for the current user and (b) at least one predetermined EID vector for the authorized user to determine whether the current user is the authorized user; and (iii) in response to determining that the current user is the authorized user, use the master ECG identifier for the authorized user and the secret chip key for the data processing system to decrypt the ECG-encrypted data.

Example B2 is an apparatus according to Example B1, wherein the security software further enables the data processing system to save a collection of predetermined EID vectors for the authorized user, wherein said collection of predetermined EID vectors comprises the at least one predetermined EID vector for the authorized user.

Example B3 is an apparatus according to Example B2, wherein the security software further enables the data processing system to prompt the authorized user to provide ECG readings for different physical states of the authorized user, wherein the different physical states comprise a resting state and an active state. Also, the collection of predetermined EID vectors for the authorized user is based on ECG readings taken from the authorized user in the different physical states.

Example B4 is an apparatus according to Example B2, wherein the security software further enables the data processing system to (a) save the master ECG identifier for the authorized user in secure storage; (b) encrypt the collection of predetermined EID vectors for the authorized user; and (c) save the encrypted collection of predetermined EID vectors for the authorized user in the secure storage. Example B4 may also include the features of Example B3.

Example B5 is an apparatus according to Example B2, wherein the operation of using the collection of predetermined EID vectors for the authorized user to determine whether the current user is the authorized user comprises using ECG-vector correlation-difference calculations to determine whether the current user is the authorized user. Example B5 may also include the features of any one or more of Examples B3 and B4.

Example B6 is an apparatus according to Example B1, wherein the security software further enables the data processing system to (a) save a collection of predetermined EID vectors for the authorized user in secure storage; and (b) generate the master ECG identifier for the authorized user, based on the collection of predetermined EID vectors for the authorized user. Example B6 may also include the features of any one or more of Examples B2 through B5.

Example B7 is an apparatus according to Example B6, wherein the operation of generating the master ECG identifier for the authorized user, based on the collection of predetermined EID vectors for the authorized user, comprises calculating the master ECG identifier as an average of the collection of predetermined EID vectors. Example B7 may also include the features of any one or more of Examples B2 through B5.

Example B8 is an apparatus according to Example B1, wherein the operation of collecting an ECG reading for a current user of the data processing system comprises (a) receiving heartbeat signals from the current user; (b) deriving ECG information from the received heartbeat signals; and (c) generating an EID vector for the current user, based on the derived ECG information. Example B8 may also include the features of any one or more of Examples B2 through B7.

Example C1 is a method for protecting electronic data. The method comprises using (a) a master ECG identifier for an authorized user of a data processing system and (b) a secret chip key for the data processing system to encrypt data in the data processing system. The method further comprise, before allowing the encrypted data to be decrypted, performing operations comprising (i) collecting at least one ECG reading for a current user of the data processing system; (ii) using (a) the collected ECG reading for the current user and (b) at least one predetermined EID vector for the authorized user to determine whether the current user is the authorized user; and (iii) in response to determining that the current user is the authorized user, using the master ECG identifier for the authorized user and the secret chip key for the data processing system to decrypt the data.

Example C2 is a method according to Example C1, and the method further comprises saving a collection of predetermined EID vectors for the authorized user. Also, the operation of using (a) the collected ECG reading for the current user and (b) at least one predetermined ECG reading for the authorized user to determine whether the current user is the authorized user comprises using the collection of predetermined EID vectors for the authorized user to determine whether the current user is the authorized user.

Example C3 is a method according to Example C2, and the method further comprises prompting the authorized user to provide ECG readings for different physical states of the authorized user, wherein the different physical states comprise a resting state and an active state. Also, the collection of predetermined EID vectors for the authorized user is based on ECG readings taken from the authorized user in the different physical states.

Example C4 is a method according to Example C2, and the method further comprises saving the master ECG identifier for the authorized user in protected storage of the data processing system. Also, the collection of predetermined EID vectors for the authorized user is also stored in the protected storage. Example C4 may also include the features of Example C3.

Example C5 is a method according to Example C2, and the operation of using the collection of predetermined EID vectors for the authorized user to determine whether the current user is the authorized user comprises using ECG-vector correlation-difference calculations to determine whether the current user is the authorized user. Example C5 may also include the features of any one or more of Example C3 and C4.

Example C6 is a method according to Example C1, and the method further comprises (a) saving, in the data processing system, a collection of predetermined EID vectors for the authorized user; and (b) generating the master ECG identifier for the authorized user, based on the collection of predetermined EID vectors for the authorized user. Example C6 may also include the features of any one or more of Examples C2 through C5.

Example C7 is a method according to Example C6, and the operation of generating the master ECG identifier for the authorized user, based on the collection of predetermined EID vectors for the authorized user, comprises calculating the master ECG identifier as an average of the collection of predetermined EID vectors. Example C7 may also include the features of any one or more of Examples C2 through C5.

Example C8 is a method according to Example C1, and the operation of collecting an ECG reading for a current user of the data processing system comprises (a) receiving heartbeat signals from the current user; (b) deriving ECG information from the received heartbeat signals; and (c) generating an EID vector for the current user, based on the derived ECG information. Example C8 may also include the features of any one or more of Examples C2 through C7.

Example D is at least one machine-accessible medium comprising computer instructions for protecting electronic data, wherein the computer instructions, in response to being executed on a data processing system, enable the data processing system to perform a method according to any of Examples C1 through C8.

Example E is a data processing system with support for protection of electronic data. The data processing system comprises: (a) a processing element; (b) at least one machine-accessible medium responsive to the processing element; and (c) computer instructions stored at least partially in the at least one machine-accessible medium, wherein the computer instructions, in response to being executed, enable the data processing system to perform a method according to any of Examples C1 through C8.

Example F is a data processing system with support for protecting electronic data. The data processing system comprises means for performing the method of any of Examples C1 through C8.

What is claimed is:

1. A data processing system to support protection of electronic data, the data processing system comprising:
   one or more electrodes capable of receiving heartbeat signals from a user of the data processing system;
   a processor in communication with the electrodes;
   external storage responsive to the processor; and
   security software which, when executed by the processor, enables the data processing system to:
   use (a) a master electrocardiogram (ECG) identifier for an authorized user of the data processing system and (b) a secret chip key for the data processing system to generate ECG-encrypted data;
   store the ECG-encrypted data in the external storage; and
   in response to a request for a decrypted version of the ECG-encrypted data:
   use the one or more electrodes to collect at least one ECG reading for a current user of the data processing system;
   use (a) the at least one collected ECG reading for the current user and (b) at least one predetermined ECG identifier (EID) vector of a collection of predetermined EID vectors for the authorized user to determine whether the current user is the authorized user, wherein the collection of predetermined EID vectors is based on ECG readings taken from the authorized user in different physical states; and
   in response to determining that the current user is the authorized user, use the master ECG identifier for the authorized user and the secret chip key for the data processing system to decrypt the ECG-encrypted data.

2. A data processing system according to claim 1, wherein the security software further enables the data processing system to:
   save the collection of predetermined EID vectors for the authorized user.

3. A data processing system according to claim 2, wherein:
   the security software further enables the data processing system to prompt the authorized user to provide ECG readings for the different physical states of the authorized user, wherein the different physical states comprise a resting state and an active state.

4. A data processing system according to claim 2, wherein:
   the data processing system further comprises secure storage responsive to the processor; and the security software further enables the data processing system to:
save the master ECG identifier for the authorized user in the secure storage;
encrypt the collection of predetermined EID vectors for the authorized user; and
save the encrypted collection of predetermined EID vectors for the authorized user in the secure storage.

5. A data processing system according to claim 2, wherein to use (a) the at least one collected ECG reading for the current user and (b) the at least one predetermined ECG identifier (EID) vector for the authorized user to determine whether the current user is the authorized user comprises:
to use ECG-vector correlation-difference calculations to determine whether the current user is the authorized user.

6. A data processing system according to claim 1, wherein:
the data processing system further comprises secure storage responsive to the processor; and
the security software further enables the data processing system to:
save, in the secure storage, the collection of predetermined EID vectors for the authorized user; and
generate the master ECG identifier for the authorized user, based on the collection of predetermined EID vectors for the authorized user.

7. A data processing system according to claim 6, wherein the operation of generating the master ECG identifier for the authorized user, based on the collection of predetermined EID vectors for the authorized user, comprises:
calculating the master ECG identifier as an average of the collection of predetermined EID vectors.

8. A data processing system according to claim 1, wherein the operation of using the one or more electrodes to collect at least one ECG reading for a current user of the data processing system comprises:
receiving heartbeat signals from the current user;
deriving ECG information from the received heartbeat signals; and
generating an EID vector for the current user, based on the derived ECG information.

9. A data processing system according to claim 1, wherein the processor is configured to prevent host software from reading the secret chip key.

10. An apparatus with support for protection of electronic data, the apparatus comprising:
a non-transitory machine accessible medium; and
security software in the machine accessible medium which, when accessed by a processor of a data processing system, enables the data processing system to:
use (a) a master electrocardiogram (ECG) identifier for an authorized user of the data processing system and (b) a secret chip key for the data processing system to generate ECG-encrypted data;
store the ECG-encrypted data in external storage; and
in response to a request for a decrypted version of the ECG-encrypted data:
collect at least one ECG reading for a current user of the data processing system;
use (a) the at least one collected ECG reading for the current user and (b) at least one predetermined ECG identifier (EID) vector of a collection of predetermined EID vectors for the authorized user to determine whether the current user is the authorized user, wherein the collection of predetermined HD vectors is based on ECG readings taken from the authorized user in different physical states; and
in response to determining that the current user is the authorized user, use the master ECG identifier for the authorized user and the secret chip key for the data processing system to decrypt the ECG-encrypted data.

11. An apparatus according to claim 10, wherein:
the security software further enables the data processing system to save the collection of predetermined EID vectors for the authorized user.

12. An apparatus according to claim 11, wherein:
the security software further enables the data processing system to prompt the authorized user to provide ECG readings for the different physical states of the authorized user, wherein the different physical states comprise a resting state and an active state.

13. An apparatus according to claim 11, wherein the security software further enables the data processing system to:
save the master ECG identifier for the authorized user in secure storage;
encrypt the collection of predetermined EID vectors for the authorized user; and
save the encrypted collection of predetermined EID vectors for the authorized user in the secure storage.

14. An apparatus according to claim 11, wherein to use (a) the at last one collected ECG reading for the current user and (b) the at least one predetermined ECG identifier (EID) vector for the authorized user to determine whether the current user is the authorized user comprises:
to use ECG-vector correlation-difference calculations to determine whether the current user is the authorized user.

15. An apparatus according to claim 10, wherein the security software further enables the data processing system to:
save the collection of predetermined EID vectors for the authorized user in secure storage; and
generate the master ECG identifier for the authorized user, based on the collection of predetermined EID vectors for the authorized user.

16. An apparatus according to claim 15, wherein the operation of generating the master ECG identifier for the authorized user, based on the collection of predetermined EID vectors for the authorized user, comprises:
calculating the master ECG identifier as an average of the collection of predetermined EID vectors.

17. An apparatus according to claim 10, wherein the operation of collecting at least one ECG reading for a current user of the data processing system comprises:
receiving heartbeat signals from the current user;
deriving ECG information from the received heartbeat signals; and
generating an EID vector for the current user, based on the derived ECG information.

18. A method for protecting electronic data, the method comprising:
using (a) a master electrocardiogram (ECG) identifier for an authorized user of a data processing system and (b) a secret chip key for the data processing system to encrypt data in the data processing system; and
before allowing the encrypted data to be decrypted, performing operations comprising:
collecting at least one ECG reading for a current user of the data processing system;

using (a) the at least one collected ECG reading for the current user and (b) at least one predetermined ECG identifier (EID) vector of a collection of predetermined EID vectors for the authorized user to determine whether the current user is the authorized user, wherein the collection of predetermined EID vectors is based on ECG readings taken from the authorized user in different physical states; and in response to determining that the current user is the authorized user, using the master ECG identifier for the authorized user and the secret chip key for the data processing system to decrypt the data.

19. A method according to claim 18, further comprising:
saving the collection of predetermined EID vectors for the authorized user; and
wherein the operation of using (a) the at least one collected ECG reading for the current user and (b) at least one predetermined ECG reading for the authorized user to determine whether the current user is the authorized user comprises:
using the collection of predetermined EID vectors for the authorized user to determine whether the current user is the authorized user.

20. A method according to claim 19, further comprising:
prompting the authorized user to provide ECG readings for the different physical states of the authorized user, wherein the different physical states comprise a resting state and an active state.

21. A method according to claim 19, further comprising:
saving the master ECG identifier for the authorized user in protected storage of the data processing system; and
wherein the collection of predetermined EID vectors for the authorized user is also stored in the protected storage.

22. A method according to claim 19, wherein the operation of using the collection of predetermined EID vectors for the authorized user to determine whether the current user is the authorized user comprises:
using ECG-vector correlation-difference calculations to determine whether the current user is the authorized user.

23. A method according to claim 18, further comprising:
saving, in the data processing system, the collection of predetermined EID vectors for the authorized user; and
generating the master ECG identifier for the authorized user, based on the collection of predetermined EID vectors for the authorized user.

24. A method according to claim 23, wherein the operation of generating the master ECG identifier for the authorized user, based on the collection of predetermined EID vectors for the authorized user, comprises:
calculating the master ECG identifier as an average of the collection of predetermined EID vectors.

25. A method according to claim 18, wherein the operation of collecting an ECG reading for a current user of the data processing system comprises:
receiving heartbeat signals from the current user;
deriving ECG information from the received heartbeat signals; and
generating an EID vector for the current user, based on the derived ECG information.

* * * * *